United States Patent [19]

Sekine et al.

[11] 4,072,697

[45] Feb. 7, 1978

[54] METHOD FOR DEODORIZING LIQUID LANOLIN

[75] Inventors: Hisashi Sekine, Mitsukaido; Akira Yamamoto, Funabashi; Shizuo Hayashi, Saitama, all of Japan

[73] Assignee: Kao Soap Co., Ltd., Tokyo, Japan

[21] Appl. No.: 676,738

[22] Filed: Apr. 14, 1976

[30] Foreign Application Priority Data

June 16, 1975 Japan ................................ 50-72935

[51] Int. Cl.[2] ................................................ C07J 9/00

[52] U.S. Cl. ............................ 260/397.25; 260/412.8; 260/428.5

[58] Field of Search .............. 260/428.5, 412.8, 397.25

[56] References Cited

U.S. PATENT DOCUMENTS

| | | | |
|---|---|---|---|
| 1,371,342 | 3/1921 | Bollman | 260/428.5 |
| 2,345,097 | 3/1944 | Buxton | 260/428.5 |
| 2,357,881 | 9/1944 | Dombrow | 260/428.5 |
| 2,629,723 | 2/1953 | Lundgren et al. | 260/412.8 |
| 3,826,720 | 7/1974 | Lowrey | 260/428.5 |

*Primary Examiner*—Winston A. Douglas
*Assistant Examiner*—John F. Niebling
*Attorney, Agent, or Firm*—Blanchard, Flynn, Thiel, Boutell & Tanis

[57] ABSTRACT

Liquid lanolin is deodorized by mixing it with a solvent selected from methanol, ethanol, mixtures of methanol and ethanol, or aqueous solutions of methanol and/or ethanol, and then separating and removing the solvent phase. A subsequent water-washing treatment provides a further improved deodorizing effect.

6 Claims, No Drawings

METHOD FOR DEODORIZING LIQUID LANOLIN

BACKGROUND OF THE INVENTION

1. FIELD OF THE INVENTION

This invention relates to a method for deodorizing liquid lanolin. More particularly, the present invention provides a method for removing unpleasant animal odor-causing substances for liquid lanolin, which liquid lanolin is obtained by purifying and dehydrating wool fat. The invention provides liquid lanolin of high quality having a high commercial value.

2. DESCRIPTION OF THE PRIOR ART

Lanolin is obtained by purifying and dehydrating wool fat that is present as a deposit on wool fibers. Lanolin is a wax that melts at a temperature approximating the body temperature of humans and it exhibits excellent skin-permeating and emollient effects. Accordingly, it is widely used as an ingredient of skin creams, skin lotions, hair creams and various other cosmetic and perfume products, and as an ointment base. Liquid lanolin is prepared from lanolin by (1) fractional crystallization from a solvent, (2) removal of high-melting-point waxes by addition of urea and (3) vacuum distillation. Liquid lanolin prepared by removing high-melting-point waxes from lanolin has excellent skin-permeating and emollient effects, like those of lanolin. As commercially available liquid lanolin products, there can be mentioned "Viscolan" (manufactured by American Cholesterol Col.) "Fluilan" (manufactured by Chroda Co.) and "Belbelan" (manufactured by Nippon Lanolin Kogyo Co.). The cloud points and solidfying points of typical commercially available lanolin and liquid lanolin are as follows:

| | Lanolin | Liquid Lanolin |
|---|---|---|
| Cloud Point (° C) | 42–46 | 17–18 |
| Solidifying Point (° C) | 36–40 | 3–4 |

Since liquid lanolin is used especially for toiletries, cosmetics, and the like, it is desired to remove unpleasant smells from liquid lanolin.

As methods for deodorizing liquid lanolin, there are known a method for purifying liquid lanolin by adsorption using calcium sulfate, a method in which liquid lanolin in the form of a thin film and under a reduced pressure of several mm Hg is contacted with water vapor flowing countercurrent thereto, a molecular distillation method, and the like. However, each of these known methods is disadvantageous because large-size equipment is required for practicing the method, the cost is high and the deodorizing effect is insufficient.

SUMMARY OF THE INVENTION

We discovered that an excellent deodorizing effect is obtained when a polar solvent selected from the group consisting of methanol, ethanol, and mixtures thereof, is mixed and agitated with liquid lanolin under specific conditions. The odor-causing components are effectively dissolved and transferred into the polar solvent phase. A deodorized liquid lanolin of high quality can be obtained by separating the polar solvent phase from the liquid lanolin phase. Based on this discovery, we have now completed the present invention.

More specifically, in accordance with the present invention, there is provided a method for deodorizing liquid lanolin characterized by using as a solvent methanol, ethanol, or mixtures thereof, or an aqueous solution containing at least 50% by weight of methanol, ethanol or mixtures thereof, mixing and agitating liquid lanolin and the solvent at a solvent/liquid lanolin weight ratio of from 0.5/1.0 to 4.0/1.0 and at an elevated temperature of from 40° to 80° C, then separating and removing the solvent phase and, if necessary, adding a suitable amount of water to the remaining liquid lanolin, mixing and agitating them at an elevated temperature of from 40° to 100° C, and then separating and removing the aqueous phase.

The deodorizing method of the present invention utilizes, in principle, the difference of the affinity of the odor-causing components between the solvent and liquid lanolin. However, the final and collective deodorizing effect cannot be predicted only by such difference of affinity, but rather it is greatly influenced by such factors as the ease of separation of the odor component-solvent phase from the liquid lanolin and the means and conditions for effecting such separation. The present invention has been completed after taking into consideration all of these factors comprehensively.

As the solvent that can be used in the present invention, there can be mentioned methanol, ethanol, mixtures thereof and aqueous solutions thereof having a concentration of at least 50% by weight. Alcohols having 3 or more carbon atoms, such as isopropyl alcohol and n-butyl alcohol, have a high solubility to liquid lanolin and they dissolve liquid lanolin homogeneously. Therefore, separation of odor components is impossible. Thus, alcohols having 3 or more carbon atoms cannot be used in the present invention. Further, since various other organic solvents such as n-hexane, chloroform, diethyl ketone, dimethyl ketone, diethyl ether and the like also dissolve liquid lanolin homogeneously, they cannot be used in the present invention. In view of the deodorizing effect, methanol is the most preferred solvent for the purposes of this invention. Since a small amount of ethanol remains dissolved in the liquid lanolin after treatment, the deodorizing effect achieved by the use of ethanol is a little inferior to the effect attained by the use of methanol. The use of an aqueous solution of such alcohol is preferred, because the amount of the alcohol that remains in the treated liquid lanolin is reduced. The weight ratio of the solvent to liquid lanolin (herein referred to as "solvent ratio"), is from 0.5 to 4.0, preferably from 1.0 to 2.0. At a solvent ratio lower than 0.5, a sufficient deodorizing effect cannot be attained, while at a solvent ratio higher than 4.0 the amount of the solvent that dissolves and remains in the liquid lanolin increases and the deodorizing effect is reduced. Further, in the latter case, economic disadvantages occur as regards the recovery of the solvent and the like.

In the present invention, liquid lanolin and the solvent are heated at 40° to 80° C and they are mixed with agitation. Then, the solvent phase is separated from the liquid lanolin phase and is removed therefrom. The mixing under agitation is generally conducted for 10 to 60 minutes. The change of the viscosity of a mixture of liquid lanolin and the solvent in response to temperature is hyperbolic. The viscosity is drastically increased when the temperature is lower than the critical level of about 40° C. For example, the viscosity of liquid lanolin at 25° C is about 2,000 to about 2,500 cp, but it is about 250 cp at 50° C. Therefore, at temperatures lower than 40° C, phase separation of liquid lanolin and the solvent is very difficult, and the amount of the solvent left in the liquid lanolin increases and the deodorizing effect is drastically lowered. For example, when the deodorizing treatment is conducted at 50° C, using methanol as the solvent, and the resulting mixture is allowed to stand still at 25° C, 8 to 10 hours are required for completion of the phase separation and, indeed, complete separation cannot be attained. However, if the mixture is maintained at 50° C after the deodorizing treatment, it separates completely into two phases within 2 to 3 hours. Various conventional procedures can be adopted for effecting separation and removal of the solvent, but in general, settling separation and centrifugal separation methods are employed. The deodorizing effect can be further improved by repeating the above procedures two or more times, and in this case, the solvent ratio in each individual stage can be less than 0.5, although the overall solvent ratio for the sum of the stages should be at least 0.5.

Deodorized liquid lanolin can be obtained according to the foregoing method. When the thus-deodorized liquid lanolin is subjected to a water washing treatment in the following manner in order to remove the odor component-containing solvent left in the liquid lanolin, liquid lanolin of much higher quality can be obtained. More specifically, the separated liquid lanolin is mixed with a suitable amount of water and the mixture is agitated at an elevated temperature of 40° to 100° C. Then, at the same elevated temperature, the aqueous phase is separated from the liquid lanolin phase and it is removed therefrom. The amount of water used for washing is not particularly critical, but it is generally 1.0 to 10 times the amount of the liquid lanolin on a weight basis. It is necessary that the system should be heated at 40° to 100° C during the water washing and separating steps. If the temperature is lower than 40° C, the separation effect is drastically lowered as in the case of the above-mentioned solvent treatment.

The thus-treated liquid lanolin is deodorized sufficiently and it is substantially odorless, and no quality degradation is observed. As is seen from the foregoing description, liquid lanolin can be deodorized relatively simply at a low cost according to the method of the present invention, and a more valuable product for toiletries, cosmetics and the like can easily be obtained.

The present invention will now be further described in detail by reference to the following illustrative Examples.

EXAMPLE 1

Various solvents, as indicated in Table 1, were mixed and agitated with liquid lanolin sufficiently under the conditions set forth in Table 1, and then the mixture was allowed to stand still. The liquid lanolin phase was separated from the solvent phase and was recovered to obtain deodorized liquid lanolin.

Table 1

| | | Deodorizing Conditions | | | |
|---|---|---|---|---|---|
| Run No. | Solvent | Solvent Ratio (liquid lanolin:solvent) | Temperature (° C) | Agitation Time (min.) | Time Required for Separation by Standing Still |
| 1 | water | 1 : 0.5 | 25 | 30 | not separated* |
| 2 | methanol | 1 : 0.5 | 25 | 30 | about 10 hours |
| 3 | ethanol | 1 : 0.5 | 25 | 30 | about 10 hours |
| 4 | isopropanol | 1 : 0.5 | 25 | 30 | not separated |
| 5 | acetone | 1 : 0.5 | 25 | 30 | not separated |
| 6 | diethyl ether | 1 : 0.5 | 25 | 30 | not separated |
| 7 | n-hexane | 1 : 0.5 | 25 | 30 | not separated |
| 8 | methanol | 1 : 0.5 | 50 | 30 | about 2 hours |
| 9 | ethanol | 1 : 0.5 | 50 | 15 | about 1 hour** |
| 10 | methanol | 1 : 1 | 80 | 15 | about 2 hours |
| 11 | methanol | 1 : 2 | 80 | 15 | about 2 hours |
| 12 | aqueous solution of methanol (50%) | 1 : 1 | 80 | 15 | about 2 hours |
| 13 | aqueous solution of ethanol (50%) | 1 : 1 | 80 | 15 | about 2 hours |
| 14 | methanol (twice treated) | 1 : 0.5 | 50 | 15 | about 2 hours |
| 15 | ethanol (twice treated) | 1 : 0.5 | 50 | 15 | about 2 hours |

Notes:
*a highly viscous emulsion was formed and separation was impossible
**the temperature was 30° C The smell of each of the thus-treated liquid lanolins was evaluated and the results shown in Table 2 were obtained. For comparison, the smell of liquid lanolin deodorized according to the conventional deodorizing method using steam in vacuo was also treated, and the results for this treatment are also shown in Table 2.

The conventional deodorizing method using water vapor in vacuo were conducted in the following manner:

Liquid lanolin was flowed down at a rate of about 150 Kg/hr.m$^2$ in the form of a thin film along the inner wall of a cylindrical vessel maintained under a pressure of 5.0 mm Hg. Simultaneously, the system was heated at about 110° C and steam was blown in from the lower portion of the vessel at a rate of about 20 Kg/hr.m$^2$ and contacted with the liquid lanolin to effect deodorization.

Table 2

| | Deodorizing Effect | | | |
|---|---|---|---|---|
| | Change of Smell | | | |
| Run No. | before treatment | after treatment | Judgment | Average Yield (%) |
| 1 | strong animal smell | considerable smell | X | not separated |
| 2 | " | slight smell | Δ ~ X | 96.6% |
| 3 | " | considerable smell | X | 93.8 |
| 4 | " | — | — | not separated |
| 5 | " | — | — | " |
| 6 | " | — | — | " |
| 7 | " | — | — | " |
| 8 | " | little smell | ○ | 96.0 |

Table 2-continued

| Run No. | Deodorizing Effect: Change of Smell: before treatment | after treatment | Judgment | Average Yield (%) |
|---|---|---|---|---|
| 9 | " | " | Δ ~ ○ | 92.0 |
| 10 | " | odorless | ◎ | 95.0 |
| 11 | " | " | ◎ | 92.0 |
| 12 | " | little smell | ○ | 96.0 |
| 13 | " | slight smell | Δ | 93.0 |
| 14 | " | odorless | ◎ | 93.0 |
| 15 | " | substantially odorless | ○ ~ ◎ | 85.0 |
| 16* | " | slight smell | Δ | — |

*conventional vacuum-steam method
In the foregoing table,
X means poor results
Δ means fair results
○ means good results
◎ means excellent results As is apparent from the foregoing results, when water is used as the solvent (Run No. 1), no deodorizing effect was obtained. When solvents other than methanol and ethanol are employed (Runs Nos. 4 to 7), since homogeneous solutions are formed, these solvents cannot be used for the method of the present invention. Even when methanol or ethanol is used as the solvent, if the treatment temperature is lower than 40° C (Runs Nos. 2 and 3), a considerable time is required for phase separation and complete separation cannot be attained. Further, the deodorizing effect is insufficient. In contrast, when the deodorizing treatment is carried out under the conditions of the present invention (Runs Nos. 8 to 15), a good deodorizing effect is obtained, and the best results are obtained when the solvent ratio is within the range of from 1 to 2 or when the same procedures are repeated twice (twice heated) even if the solvent ratio is 0.5. Example 2

The deodorized liquid lanolins obtained in Example 1 (exclusive of those obtained in Runs Nos. 1 and 4 to 7) were subjected to a water washing treatment under conditions indicated in Table 3. After the water washing treatment, each of the resulting mixtures was subjected to centrifugal separation to separate the liquid lanolin phase from the aqueous phase. The aqueous phase was removed from the liquid lanolin phase to obtain deodorized liquid lanolin. The smell of the resulting liquid lanolin was judged according to the scale mentioned in Table 2. The results are shown in Table 3.

Table 3

| Run No. | Results of Water Washing Treatment: Water Washing Conditions: liquid lanolin : washing water | Temperature (° C) | Agitation time (min) | Judgment: before washing | after washing |
|---|---|---|---|---|---|
| 2 | 1 : 5 | 80 | 30 | Δ ~ X | Δ |
| 3 | 1 : 10 | 80 | 30 | X | Δ |
| 8 | 1 : 5 | 80 | 30 | ○ | ◎ |
| 9 | 1 : 10 | 80 | 30 | Δ ~ ○ | ○ |
| 10 | 1 : 5 | 80 | 30 | ◎ | ◎ |
| 11 | 1 : 5 | 80 | 30 | ◎ | ◎ |
| 12 | 1 : 5 | 80 | 30 | ○ | ○ ~ ◎ |
| 13 | 1 : 10 | 80 | 30 | Δ | ○ |
| 14 | 1 : 5 | 80 | 30 | ◎ | ◎ |
| 15 | 1 : 5 | 80 | 30 | ○ ~ ◎ | ◎ |
| 16 | 1 : 10 | 80 | 30 | Δ | Δ |

As is apparent from the foregoing results, even when the deodorizing effect by the solvent treatment is relatively insufficient, if the water washing treatment is carried out after the solvent treatment, a product which is substantially odorless can be obtained.

The embodiments of the invention in which an exclusive property or privilege is claimed are defined as follows:

1. A method for deodorizing liquid lanolin having a cloud point of about 17°-18° C and a solidifying point of about 3°-4° C, which consists essentially of the steps of adding to liquid lanolin containing odor-causing substances and mixing uniformly therein a solvent for said odor-causing substances selected from the group consisting of methanol, ethanol, mixtures of methanol and ethanol, and aqueous solutions thereof containing up to 50% by weight of water, the weight ratio of said solvent to said liquid lanolin being in the range of from 0.5/1.0 to 4.0/1.0, the mixing being carried out at a temperature of from 40° to 80° C and for a period of time effective to dissolve in said solvent the odor-causing substances initially present in the liquid lanolin, then while maintaining the mixture at 40° to 80° C separating and removing the solvent phase containing the odor-causing substances dissolved therein from the liquid lanolin and thereby recovering deodorized liquid lanolin.

2. A method as claimed in claim 1 in which the weight ratio of said solvent to liquid lanolin is from 1.0/1.0 to 2.0/1.0.

3. A method as claimed in claim 1 in which said solvent is methanol.

4. A method as claimed in claim 1 in which the mixing step is carried out for about 10 to about 60 minutes.

5. A method as claimed in claim 1, wherein the solvent is added to and mixed with the liquid lanolin in two separate stages, and the solvent phase employed in the first stage is removed from the liquid lanolin and then in the second stage additional fresh solvent is added and mixed with the liquid lanolin.

6. A method as claimed in claim 1 including the additional steps of adding to the deodorized liquid lanolin and mixing uniformly therein from one to 10 parts by weight of water, per one part by weight of deodorized lanolin, at a temperature of 40° to 100° C for a period of time effective to dissolve in the water any solvent that remains in the deodorized liquid lanolin, then while maintaining the latter mixture at 40° to 100° C, separating and removing the water phase and thereby recovering additionally deodorized lanolin.

* * * * *